(12) United States Patent
Gorochow

(10) Patent No.: US 12,064,363 B2
(45) Date of Patent: *Aug. 20, 2024

(54) SELF-EXPANDING DEVICE DELIVERY APPARATUS WITH DUAL FUNCTION BUMP

(71) Applicant: DePuy Synthes Products, Inc., Raynham, MA (US)

(72) Inventor: Lacey Gorochow, Miami, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 220 days.

This patent is subject to a terminal disclaimer.

(21) Appl. No.: 17/479,052

(22) Filed: Sep. 20, 2021

(65) Prior Publication Data
US 2022/0000646 A1    Jan. 6, 2022

Related U.S. Application Data

(63) Continuation of application No. 16/394,318, filed on Apr. 25, 2019, now Pat. No. 11,129,738, which is a
(Continued)

(51) Int. Cl.
*A61F 2/966* (2013.01)
*A61F 2/844* (2013.01)
(Continued)

(52) U.S. Cl.
CPC .............. *A61F 2/966* (2013.01); *A61F 2/844* (2013.01); *A61F 2/86* (2013.01);
(Continued)

(58) Field of Classification Search
CPC .. A61F 2/966; A61F 2/844; A61F 2/86; A61F 2002/9534; A61F 2002/9665;
(Continued)

(56) References Cited

U.S. PATENT DOCUMENTS

| | | |
|---|---|---|
| 4,332,278 A | 6/1982 | Lalikos |
| 4,610,688 A | 9/1986 | Silvestrini |

(Continued)

FOREIGN PATENT DOCUMENTS

| | | |
|---|---|---|
| CN | 101234046 A | 8/2008 |
| CN | 101677867 A | 3/2010 |

(Continued)

OTHER PUBLICATIONS

Ansaar T. Rai et al., "Cerebrovascular geometry in the anterior circulation: an analysis of diameter, length and the vessel taper", J NeuroIntervent Surg 2013; 5: 371-375_ doi: 10_ 1136/neurintsurg-2012-010314; Apr. 4, 2012.

(Continued)

*Primary Examiner* — Richard G Louis
(74) *Attorney, Agent, or Firm* — Troutman Pepper Hamilton Sanders LLP

(57) ABSTRACT

A self-expanding element delivery apparatus includes a catheter having an inner lumen, a self-expanding element, and a delivery wire disposed within and extending through the inner lumen and the self-expanding element. The self-expanding element has a proximal, distal, and an intermediate portion. The element has anchor members, a compressed configuration fitting within the inner lumen, and an expanded configuration dimensioned larger than the catheter. The delivery wire also has proximal and distal portions, an intermediate portion, a dual function bump member disposed approximate to the intermediate portion, and a pusher bump member disposed approximate to the proximal portion of the delivery wire. A bump member distance between the dual function bump member and the pusher bump member is such that so that only one of the dual function bump member and the pusher bump member can contact one of the anchor members.

13 Claims, 6 Drawing Sheets

Related U.S. Application Data continuation of application No. 15/281,974, filed on Sep. 30, 2016, now Pat. No. 10,292,851.

(51) Int. Cl.
 A61F 2/86 (2013.01)
 A61F 2/95 (2013.01)

(52) U.S. Cl.
 CPC .............. *A61F 2002/9534* (2013.01); *A61F 2002/9665* (2013.01); *A61F 2210/0014* (2013.01)

(58) Field of Classification Search
 CPC ...... A61F 2210/0014; A61F 2002/9505; A61F 2002/9528; A61F 2002/9511
 See application file for complete search history.

(56) References Cited

U.S. PATENT DOCUMENTS

| | | |
|---|---|---|
| 4,754,685 A | 7/1988 | Kite |
| 5,064,435 A | 11/1991 | Porter |
| 5,275,622 A | 1/1994 | Lazarus et al. |
| 5,282,824 A | 2/1994 | Gianturco |
| 5,330,500 A | 7/1994 | Song |
| 5,382,259 A | 1/1995 | Phelps et al. |
| 5,387,235 A | 2/1995 | Chuter |
| 5,423,849 A | 6/1995 | Engelson |
| 5,476,508 A | 12/1995 | Amstrup |
| 5,522,881 A | 6/1996 | Lentz |
| 5,549,662 A | 8/1996 | Fordenbacher |
| 5,556,413 A | 9/1996 | Lam |
| 5,601,593 A | 2/1997 | Freitag |
| 5,609,627 A | 3/1997 | Goicoechea |
| 5,645,558 A | 7/1997 | Horton |
| 5,662,622 A | 9/1997 | Gore |
| 5,702,418 A | 12/1997 | Ravenscroft |
| 5,725,549 A | 3/1998 | Lam |
| 5,728,131 A | 3/1998 | Frantzen |
| 5,755,772 A | 5/1998 | Evans et al. |
| 5,769,887 A | 6/1998 | Brown |
| 5,776,161 A | 7/1998 | Globerman |
| 5,817,126 A | 10/1998 | Imran |
| 5,849,037 A | 12/1998 | Frid |
| 5,851,217 A | 12/1998 | Wolff |
| 5,855,601 A | 1/1999 | Bessler |
| 5,899,935 A | 5/1999 | Ding |
| 5,916,235 A | 6/1999 | Guglielmi |
| 5,916,264 A | 6/1999 | Von Oepen |
| 5,961,546 A | 10/1999 | Robinson et al. |
| 6,010,529 A | 1/2000 | Herweck |
| 6,015,432 A | 1/2000 | Rakos et al. |
| 6,033,436 A | 3/2000 | Steinke |
| 6,036,725 A | 3/2000 | Avellanet |
| 6,051,020 A | 4/2000 | Goicoechea |
| 6,099,559 A | 8/2000 | Nolting |
| 6,110,198 A | 8/2000 | Fogarty |
| 6,123,722 A | 9/2000 | Fogarty et al. |
| 6,123,723 A | 9/2000 | Konya et al. |
| 6,152,956 A | 11/2000 | Pierce |
| 6,161,399 A | 12/2000 | Jayaraman |
| 6,165,213 A | 12/2000 | Goicoechea |
| 6,168,621 B1 | 1/2001 | Vrba |
| 6,176,875 B1 | 1/2001 | Lenker |
| 6,241,691 B1 | 6/2001 | Ferrera et al. |
| 6,264,683 B1 | 7/2001 | Stack et al. |
| 6,280,465 B1 | 8/2001 | Cryer |
| 6,319,278 B1 | 11/2001 | Quinn |
| 6,325,823 B1 | 12/2001 | Horzewski |
| 6,348,066 B1 | 2/2002 | Pinchuk et al. |
| 6,391,037 B1 | 5/2002 | Greenhalgh |
| 6,409,755 B1 | 6/2002 | Vrba |
| 6,488,702 B1 | 12/2002 | Besselink |
| 6,612,012 B2 | 9/2003 | Mitelberg et al. |
| 6,626,936 B2 | 9/2003 | Stinson |
| 6,635,080 B1 | 10/2003 | Lauterjung et al. |
| 6,673,106 B2 | 1/2004 | Mitelberg |
| 6,699,277 B1 | 3/2004 | Freidberg et al. |
| 6,740,113 B2 | 5/2004 | Vrba |
| 6,673,107 B1 | 6/2004 | Brandt |
| 6,770,089 B1 | 8/2004 | Hong et al. |
| 6,818,013 B2 | 11/2004 | Mitelberg |
| 6,833,003 B2 | 12/2004 | Jones |
| 6,899,914 B2 | 5/2005 | Schmitz |
| 6,911,040 B2 | 6/2005 | Johnson et al. |
| 6,918,928 B2 | 7/2005 | Wolinsky |
| 6,929,659 B2 | 8/2005 | Pinchuk |
| 6,945,994 B2 | 9/2005 | Austin et al. |
| 6,955,685 B2 | 10/2005 | Escamilla |
| 6,960,227 B2 | 11/2005 | Jones |
| 6,960,228 B2 | 11/2005 | Mitelberg et al. |
| 6,970,734 B2 | 11/2005 | Eidenschink |
| 7,001,422 B2 | 2/2006 | Escamilla |
| 7,037,331 B2 | 5/2006 | Mitelberg |
| 7,122,052 B2 | 10/2006 | Greenhaigh |
| 7,153,324 B2 | 12/2006 | Case |
| 7,201,769 B2 | 4/2007 | Jones et al. |
| 7,208,008 B2 | 4/2007 | Clarke |
| 7,267,685 B2 | 9/2007 | Butaric |
| 7,288,111 B1 | 10/2007 | Holloway et al. |
| 7,291,167 B2 | 11/2007 | DiCaprio |
| 7,309,351 B2 | 12/2007 | Escamilla et al. |
| 7,344,559 B2 | 3/2008 | Gray |
| 7,462,190 B2 | 12/2008 | Lombardi |
| 7,480,973 B2 | 1/2009 | Miller |
| 7,628,806 B2 | 12/2009 | Yampolsky et al. |
| 7,632,302 B2 | 12/2009 | Vreeman et al. |
| 7,641,647 B2 | 1/2010 | Gunderson |
| 7,655,031 B2 | 2/2010 | Tenne et al. |
| 7,655,034 B2 | 2/2010 | Mitchell et al. |
| 7,708,773 B2 | 5/2010 | Pinchuk et al. |
| 7,758,629 B2 | 7/2010 | Holloway et al. |
| 7,761,138 B2 | 7/2010 | Wang |
| 7,806,919 B2 | 10/2010 | Bloom et al. |
| 7,806,923 B2 | 10/2010 | Moloney |
| RE42,244 E | 3/2011 | Boatman |
| 7,913,371 B2 | 3/2011 | Klocke |
| 7,985,213 B2 | 7/2011 | Parker |
| 7,998,187 B2 | 8/2011 | Hartley et al. |
| 8,021,418 B2 | 9/2011 | Gerberding |
| 8,043,353 B2 | 10/2011 | Kaufmann et al. |
| 8,043,357 B2 | 10/2011 | Hartley |
| 8,048,139 B2 | 11/2011 | Frid et al. |
| 8,052,741 B2 | 11/2011 | Bruszewski et al. |
| 8,092,510 B2 | 1/2012 | Metcalf et al. |
| 8,142,456 B2 | 3/2012 | Rosqueta |
| 8,152,833 B2 | 4/2012 | Zaver |
| 8,182,523 B2 | 5/2012 | Tenne et al. |
| 8,187,316 B2 | 5/2012 | Kuppurathanam |
| 8,357,194 B2 | 1/2013 | Majercak |
| 8,372,133 B2 | 2/2013 | Douk et al. |
| 8,394,119 B2 | 3/2013 | Zaver |
| 8,449,600 B2 | 5/2013 | Hartley et al. |
| 8,449,604 B2 | 5/2013 | Moaddeb |
| 8,484,120 B2 | 7/2013 | Hagaman et al. |
| 8,562,666 B2 | 10/2013 | Bonsignore |
| 8,579,959 B2 | 11/2013 | Ducke |
| 8,597,276 B2 | 12/2013 | Vongphakdy et al. |
| 8,636,791 B1 | 1/2014 | Raju et al. |
| 8,641,748 B2 | 2/2014 | Hebert et al. |
| 8,672,992 B2 | 3/2014 | Orr |
| 8,709,065 B2 | 4/2014 | Chobotov |
| 8,734,501 B2 | 5/2014 | Hartley et al. |
| 8,778,008 B2 | 7/2014 | Amplatz et al. |
| 8,816,247 B1 | 8/2014 | Janardhan et al. |
| 8,864,811 B2 | 10/2014 | Kao |
| 9,078,731 B2 | 7/2015 | Mortarino |
| 9,192,462 B2 | 11/2015 | Vinluan et al. |
| 9,232,992 B2 | 1/2016 | Heidner |
| 9,301,864 B2 | 4/2016 | Kao |
| 9,320,590 B2 | 4/2016 | Zaver |
| 9,339,260 B2 | 5/2016 | Eidenschink et al. |
| 9,427,343 B2 | 8/2016 | Bogert |
| 9,532,792 B2 | 1/2017 | Galdonik et al. |

(56) References Cited

U.S. PATENT DOCUMENTS

| | | |
|---|---|---|
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,713,523 B2 | 7/2017 | Zacharias |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,787,260 B2 | 10/2017 | Lehtola |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,004,513 B2 | 6/2018 | Leopold et al. |
| 10,058,421 B2 | 8/2018 | Eberhardt et al. |
| 10,076,428 B2 | 9/2018 | Gorochow |
| 10,143,551 B2 | 12/2018 | Braido et al. |
| 10,182,927 B2 | 1/2019 | Lorenzo |
| 10,206,796 B2 | 2/2019 | Tehrani et al. |
| 10,232,564 B2 | 5/2019 | Pelled |
| 10,292,851 B2 | 5/2019 | Gorochow |
| 10,321,991 B2 | 6/2019 | Glimsdale |
| 10,561,509 B2 | 2/2020 | Slazas et al. |
| 10,821,008 B2 | 11/2020 | Gorochow |
| 2001/0021873 A1 | 9/2001 | Stinson |
| 2001/0025195 A1 | 9/2001 | Shaolian |
| 2001/0049554 A1 | 12/2001 | Ruiz et al. |
| 2002/0095205 A1 | 7/2002 | Edwin |
| 2002/0111671 A1 | 8/2002 | Stenzel |
| 2002/0151953 A1 | 10/2002 | Chobotov |
| 2002/0151956 A1 | 10/2002 | Chobotov |
| 2002/0188344 A1 | 12/2002 | Bolea |
| 2002/0198587 A1 | 12/2002 | Greenberg et al. |
| 2003/0009211 A1 | 1/2003 | DiCarlo |
| 2003/0055493 A1 | 3/2003 | Carpenter |
| 2003/0114922 A1 | 6/2003 | Iwasaka |
| 2003/0144725 A1 | 7/2003 | Lombardi |
| 2003/0225448 A1 | 12/2003 | Gerberding |
| 2004/0015229 A1 | 1/2004 | Fulkerson |
| 2004/0024416 A1 | 2/2004 | Yodfat et al. |
| 2004/0044399 A1 | 3/2004 | Ventura |
| 2004/0073291 A1 | 4/2004 | Brown |
| 2004/0167619 A1 | 8/2004 | Case |
| 2004/0236406 A1 | 11/2004 | Gregorich |
| 2004/0254637 A1 | 12/2004 | Vang |
| 2005/0010281 A1 | 1/2005 | Yodfat et al. |
| 2005/0033406 A1 | 2/2005 | Barnhart |
| 2005/0043784 A1 | 2/2005 | Yampolsky et al. |
| 2005/0049668 A1 | 3/2005 | Jones et al. |
| 2005/0049669 A1 | 3/2005 | Jones et al. |
| 2005/0049670 A1 | 3/2005 | Jones |
| 2005/0125051 A1 | 6/2005 | Eidenschink |
| 2005/0131516 A1 | 6/2005 | Greenhalgh |
| 2005/0137682 A1 | 6/2005 | Justino |
| 2005/0148866 A1 | 7/2005 | Gunderson |
| 2005/0228484 A1 | 10/2005 | Stephens et al. |
| 2005/0234536 A1 | 10/2005 | Mitelberg |
| 2005/0257674 A1 | 11/2005 | Nishri et al. |
| 2005/0283220 A1 | 12/2005 | Gobran |
| 2005/0288775 A1 | 12/2005 | Dong |
| 2006/0015173 A1 | 1/2006 | Clifford |
| 2006/0064151 A1 | 3/2006 | Guterman |
| 2006/0064156 A1 | 3/2006 | Thistle |
| 2006/0069424 A1 | 3/2006 | Acosta |
| 2006/0195175 A1 | 8/2006 | Bregulla |
| 2006/0206202 A1 | 9/2006 | Bonhoeffer et al. |
| 2006/0212113 A1 | 9/2006 | Shaolian et al. |
| 2006/0271153 A1 | 11/2006 | Garcia |
| 2006/0271165 A1 | 11/2006 | Yip et al. |
| 2006/0287717 A1 | 12/2006 | Rowe |
| 2007/0005127 A1 | 1/2007 | Boekstegers |
| 2007/0043432 A1 | 2/2007 | Perouse |
| 2007/0060994 A1 | 3/2007 | Gobran |
| 2007/0100427 A1 | 5/2007 | Perouse |
| 2007/0156230 A1 | 7/2007 | Dugan |
| 2007/0167955 A1 | 7/2007 | Arnault De La Menardiere et al. |
| 2007/0191922 A1 | 8/2007 | Hartley |
| 2007/0203503 A1 | 8/2007 | Salahieh |
| 2007/0208373 A1 | 9/2007 | Zaver et al. |
| 2007/0208409 A1 | 9/2007 | Quigley |
| 2007/0213810 A1 | 9/2007 | Newhauser |
| 2007/0219612 A1 | 9/2007 | Andreas |
| 2007/0219613 A1 | 9/2007 | Kao |
| 2007/0233223 A1 | 10/2007 | Styrc |
| 2007/0233224 A1 | 10/2007 | Leynov |
| 2007/0233228 A1 | 10/2007 | Eberhardt et al. |
| 2007/0238979 A1 | 10/2007 | Huynh |
| 2007/0255385 A1 | 11/2007 | Tenne et al. |
| 2008/0009934 A1 | 1/2008 | Schneider et al. |
| 2008/0009938 A1 | 1/2008 | Huang |
| 2008/0071307 A1 | 3/2008 | DeBruyne et al. |
| 2008/0140172 A1 | 6/2008 | Carpenter |
| 2008/0221664 A1 | 9/2008 | Bales et al. |
| 2008/0221670 A1 | 9/2008 | Clerc |
| 2008/0243227 A1 | 10/2008 | Lorenzo |
| 2008/0281350 A1 | 11/2008 | Sepetka |
| 2008/0288046 A1 | 11/2008 | Hemerick |
| 2009/0005848 A1 | 1/2009 | Strauss |
| 2009/0030501 A1 | 1/2009 | Morris |
| 2009/0076594 A1 | 3/2009 | Sabaria |
| 2009/0082844 A1 | 3/2009 | Zacharias |
| 2009/0082845 A1 | 3/2009 | Chobotov |
| 2009/0082847 A1 | 3/2009 | Zacharias |
| 2009/0163951 A1 | 6/2009 | Simmons |
| 2009/0192588 A1 | 7/2009 | Shin |
| 2009/0198315 A1 | 8/2009 | Boudjemline |
| 2009/0234429 A1 | 9/2009 | Lau |
| 2009/0248133 A1 | 10/2009 | Bloom |
| 2009/0287145 A1 | 11/2009 | Cragg |
| 2009/0297582 A1 | 12/2009 | Meyer et al. |
| 2009/0306761 A1 | 12/2009 | Hebert et al. |
| 2009/0326640 A1 | 12/2009 | Yoshimura |
| 2010/0010619 A1 | 1/2010 | Tischler |

(56) References Cited

U.S. PATENT DOCUMENTS

| | | |
|---|---|---|
| 2010/0010622 A1 | 1/2010 | Lowe |
| 2010/0069948 A1 | 3/2010 | Veznedaroglu |
| 2010/0161028 A1 | 6/2010 | Chuter |
| 2010/0161036 A1 | 6/2010 | Pintor |
| 2010/0234935 A1 | 9/2010 | Bashiri |
| 2010/0249815 A1 | 9/2010 | Jantzen |
| 2010/0274282 A1 | 10/2010 | Olson |
| 2010/0292777 A1 | 11/2010 | Meyer |
| 2010/0298872 A1 | 11/2010 | Berndt |
| 2010/0324649 A1 | 12/2010 | Mattsson |
| 2010/0324651 A1 | 12/2010 | Holzer |
| 2010/0331972 A1 | 12/2010 | Pintor |
| 2011/0004237 A1 | 1/2011 | Schneider et al. |
| 2011/0060400 A1 | 3/2011 | Oepen |
| 2011/0137397 A1 | 6/2011 | Chan et al. |
| 2011/0184508 A2 | 7/2011 | Burmeister |
| 2011/0264186 A1 | 10/2011 | Berglung et al. |
| 2011/0307049 A1 | 12/2011 | Kao |
| 2012/0035714 A1 | 2/2012 | Ducke et al. |
| 2012/0041538 A1 | 2/2012 | White |
| 2012/0065728 A1 | 3/2012 | Galnor et al. |
| 2012/0123529 A1 | 5/2012 | Levi |
| 2012/0168022 A1 | 7/2012 | Rasmussen |
| 2012/0191176 A1 | 7/2012 | Nagl |
| 2012/0197377 A1 | 8/2012 | Ditter |
| 2012/0271403 A1 | 10/2012 | Gries |
| 2012/0283768 A1 | 11/2012 | Cox et al. |
| 2012/0296418 A1 | 11/2012 | Bonyuet |
| 2013/0041454 A1 | 2/2013 | Dobson |
| 2013/0060323 A1 | 3/2013 | McHugo |
| 2013/0123901 A1 | 5/2013 | Connor |
| 2013/0144375 A1 | 6/2013 | Giasolli |
| 2013/0245745 A1 | 9/2013 | Vong et al. |
| 2013/0253572 A1 | 9/2013 | Molaei et al. |
| 2013/0274849 A1 | 10/2013 | Zaver |
| 2013/0345739 A1 | 12/2013 | Brady |
| 2014/0025161 A1 | 1/2014 | Stankus et al. |
| 2014/0135812 A1 | 5/2014 | Divino et al. |
| 2014/0200607 A1 | 7/2014 | Sepetka et al. |
| 2014/0200648 A1 | 7/2014 | Newell et al. |
| 2014/0277332 A1 | 9/2014 | Slazas et al. |
| 2014/0277360 A1* | 9/2014 | Girnary ............... A61F 2/848 623/1.12 |
| 2014/0277376 A1 | 9/2014 | Lorenzo |
| 2014/0277400 A1 | 9/2014 | Wainwright et al. |
| 2014/0336741 A1 | 11/2014 | Connor |
| 2015/0018458 A1 | 1/2015 | Ito |
| 2015/0025625 A1 | 1/2015 | Rylski et al. |
| 2015/0045831 A1 | 2/2015 | Allen |
| 2015/0119974 A1 | 4/2015 | Rothstein |
| 2015/0148882 A1 | 5/2015 | Ma et al. |
| 2015/0265400 A1 | 9/2015 | Eidenschink |
| 2015/0320556 A1 | 11/2015 | Levi |
| 2015/0374483 A1 | 12/2015 | Janardham et al. |
| 2016/0030155 A1 | 2/2016 | Cox et al. |
| 2016/0038280 A1 | 2/2016 | Morriss |
| 2016/0058524 A1 | 3/2016 | Tehrani et al. |
| 2016/0235561 A1 | 8/2016 | Wrobel et al. |
| 2016/0302949 A1 | 10/2016 | Nishigishi |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079813 A1 | 3/2017 | Bar et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0100231 A1 | 4/2017 | Frid |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0156734 A1 | 6/2017 | Griffin |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0196689 A1 | 7/2017 | Salahieh |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265870 A1 | 9/2017 | Kealey et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281375 A1 | 10/2017 | Longo |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290653 A1 | 10/2017 | Folan et al. |
| 2017/0290654 A1 | 10/2017 | Sethna |
| 2017/0290686 A1 | 10/2017 | Sirhan |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0092766 A1 | 4/2018 | Gorochow |
| 2018/0125649 A1 | 5/2018 | Nasr |
| 2018/0263794 A1 | 9/2018 | Slazas et al. |
| 2018/0333281 A1 | 11/2018 | Tehrani et al. |
| 2019/0015229 A1 | 1/2019 | Fukutaki |
| 2019/0021888 A1 | 1/2019 | Tehrani |
| 2019/0038404 A1 | 2/2019 | Iamberger |
| 2019/0038405 A1 | 2/2019 | Iamberger |
| 2019/0053895 A1 | 2/2019 | Levi |
| 2019/0053899 A1 | 2/2019 | Levi |

(56) References Cited

U.S. PATENT DOCUMENTS

| | | |
|---|---|---|
| 2019/0224008 A1 | 7/2019 | Bressloff |
| 2022/0241097 A1 | 8/2022 | Shahriari |

FOREIGN PATENT DOCUMENTS

| | | |
|---|---|---|
| CN | 101779992 A | 7/2010 |
| CN | 102100587 A | 6/2011 |
| CN | 102271620 A | 12/2011 |
| CN | 103330605 A | 10/2013 |
| CN | 103347466 A | 10/2013 |
| CN | 104042376 A | 9/2014 |
| CN | 104042380 A | 9/2014 |
| CN | 104582643 A | 4/2015 |
| CN | 105592826 A | 5/2016 |
| CN | 105832452 A | 8/2016 |
| CN | 109662821 A | 4/2019 |
| CN | 107205736 A | 9/2019 |
| DE | 202008014828 U1 | 2/2009 |
| DE | 102011015995 A1 | 10/2012 |
| DE | 10 2014 113836 A1 | 3/2016 |
| EP | 0701800 A1 | 3/1996 |
| EP | 0894505 A2 | 2/1999 |
| EP | 1488763 A2 | 12/2004 |
| EP | 1634546 A1 | 3/2006 |
| EP | 2545887 A1 | 1/2013 |
| EP | 2 777 642 A1 | 9/2014 |
| EP | 2777638 A1 | 9/2014 |
| EP | 2777649 A1 | 9/2014 |
| EP | 2915509 A1 | 9/2015 |
| EP | 3 311 782 A1 | 4/2018 |
| FR | 2939637 A1 | 6/2010 |
| JP | 3-503246 A | 7/1991 |
| JP | 11-57010 A | 3/1999 |
| JP | 11-57020 A | 3/1999 |
| JP | 2004-267750 A | 9/2004 |
| JP | 2008-502378 A | 1/2008 |
| JP | 2013-541358 A1 | 11/2013 |
| JP | 2016-202248 A | 12/2016 |
| TW | 201716037 A | 5/2017 |
| WO | WO 1989/008433 A1 | 9/1989 |
| WO | WO 95/05132 A1 | 2/1995 |
| WO | WO 99/43379 A1 | 9/1999 |
| WO | WO 2001/015632 A1 | 3/2001 |
| WO | WO 01/35864 A1 | 5/2001 |
| WO | WO 2001/058384 A1 | 8/2001 |
| WO | WO 2001/072240 A1 | 10/2001 |
| WO | WO 2005/087138 A1 | 9/2005 |
| WO | WO 2008/130530 A1 | 10/2008 |
| WO | WO 2012/082440 A1 | 6/2012 |
| WO | WO 2012/096687 A1 | 7/2012 |
| WO | WO 2013/126299 A1 | 8/2013 |
| WO | WO 2013/151793 A1 | 10/2013 |

OTHER PUBLICATIONS mig-welding.co.uk; Excerpt from with comment of Jun. 29, 2011 on pictures of welds.

mitcale.com; Welded connections excerpt, downloaded Dec. 6, 2012.

Navigate Tough Anatomy; brochure Copyright 2009; Codman & Shurtleff, Inc., 325 Paramount Drive, Raynham, Massachusetts.

Plug Weld Joining Two Plates; Excerpt from esabna.com, downloaded Dec. 6, 2012.

\* cited by examiner

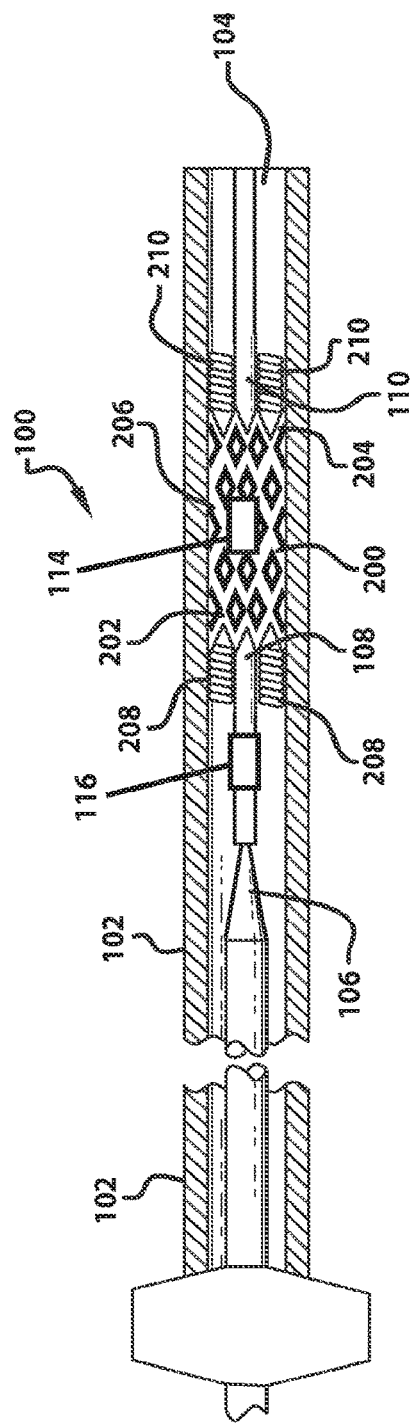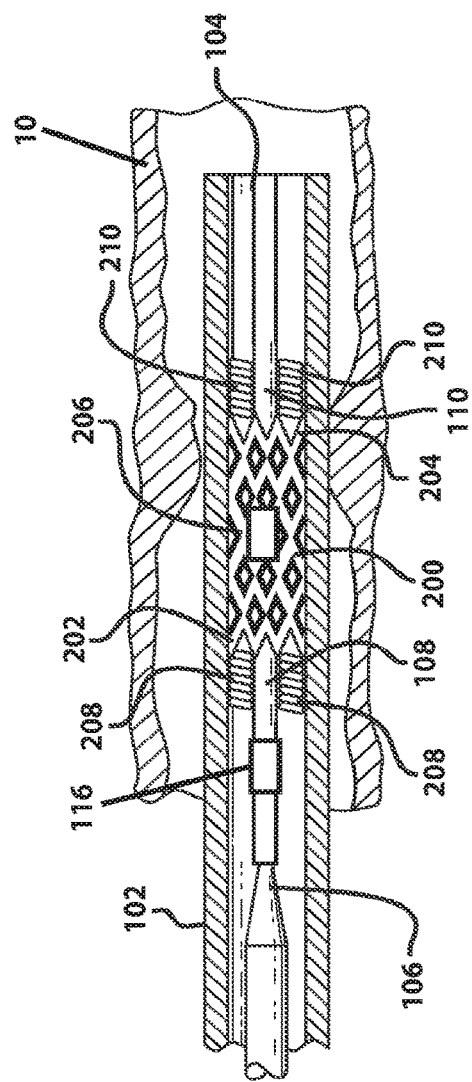

SELF-EXPANDING DEVICE DELIVERY APPARATUS WITH DUAL FUNCTION BUMP

CROSS-REFERENCE TO RELATED APPLICATIONS

This application is a continuation of U.S. patent application Ser. No. 16/394,318, filed on Apr. 25, 2019, which is a continuation of U.S. patent application Ser. No. 15/281,974, filed on Sep. 30, 2016, now issued as U.S. Pat. No. 10,292,851, each of which is incorporated herein by reference in their entirety.

FIELD OF THE INVENTION

This invention relates generally to devices for interventional therapeutic treatment or vascular surgery for treatment of defects in the vasculature, and more particularly concerns a system for delivering a self-expanding device or stent to a treatment site in a body lumen of a patient.

BACKGROUND

Cardiac stents, which are an example of a self-expanding device, are inserted into a blood vessel to provide an open path within the blood vessel, have been widely used in intravascular angioplasty treatment of occluded cardiac arteries, and in other applications. Stents are often deployed by use of inflatable balloons, or mechanical devices which force the stent open, thereby reinforcing the artery wall and provide a clear through-path in the center of the artery after the angioplasty procedure to prevent restenosis. The use of placement techniques, such as balloons or mechanical expansions of the type often found to be useful in cardiac surgery, are relatively less useful in vasoocclusive surgery, particularly when tiny vessels, such as those found in the brain, are to be treated.

Other stents are self expanding and are just deployed inside of the vascular. Their self-expanding nature allows them to be smaller as well as the devices to deploy them. There are different techniques to deploy the stents, and each has benefits and drawbacks. One expandable stent and delivery system is known that includes an expandable stent having proximal and distal anchor members mounted on proximal and distal legs extending proximally and distally from the stent. The proximal and distal anchor members of the expandable stent are mounted in gaps formed between proximal, intermediate and distal cylindrical members disposed on and spaced apart along an elongated core member. However, pushing the device distally in a catheter from the proximal end of the device is not optimal, because application of force in a distal direction on the proximal end of the stent can axially compress the stent, and can cause the stent to expand radially. Likewise, retracting the device proximally may not be optimal either, because application of force in a proximal direction on the distal end of the stent also can axially compress the stent, and can cause the stent to expand radially.

The deployment techniques fall into two categories, one is where the members are deployed outside the stent to pull or push accordingly depending on distal or proximal placement, or sometimes both. See, U.S. Pat. Nos. 6,123,723, 6,280,465, and US Publication No. 2011/0307049. Other techniques deploy the members inside of the stent. See, US Publication No. 2014/0277360, and U.S. Pat. Nos. 5,702,418, and 6,955,685. However, self-expanding device delivery systems with multiple members pose two problems:

1) After the physician has deployed the self-expanding device, he/she must re-sheathe the delivery wire back into the microcatheter, to then dispose of the wire. When recapturing the delivery wire, the members of the delivery system can get caught on the deployed device and can subsequently alter the position of the device in the anatomy. The more members on the wire, the more often this can happen.
2) The more members on the delivery wire, the more difficult it is to manufacture. In order to build the delivery system, a manufacturer can either secure polymer/metal sleeves onto a core wire or grind down a core wire to create members on a wire. The more members on a delivery wire, the more material must be used to add and secure members, or the more the grind profile has to change to accommodate all of the members.

Thus, would be desirable to provide a delivery system for expandable stents that offers the flexibility of engaging the device and for pushing and/or pulling the device proximally or distally as desired. Also desirable is a simplified manufacturing method.

SUMMARY

The dual function delivery system described below reduces these two problems by combining certain members into one. This invention provides a unique advantage of a delivery system that includes one feature that can perform two functions.

Thus, a self-expanding element delivery apparatus can include a catheter having an inner lumen, a self-expanding element, and a delivery wire disposed within and extending through the inner lumen and the self-expanding element. The self-expanding element has a proximal end, a distal end, an intermediate portion between the proximal and distal ends, and a proximal and distal anchor member disposed accordingly. The element is configured to have a compressed configuration dimensioned to fit within the inner lumen of the catheter, and an expanded configuration dimensioned larger than the catheter. The self-expanding element is in the compressed configuration when disposed within the inner lumen, and is in the expanded configuration when disposed outside the inner lumen. The delivery wire also has a proximal and distal portions, an intermediate portion located between, a dual function bump member disposed approximate to the intermediate portion of the delivery wire, and a pusher bump member disposed approximate to the proximal portion of the delivery wire. There can be a bump member distance between the dual function bump member and the pusher bump member so that only one of the dual function bump member and the pusher bump member can contact one of distal anchor member and the proximal anchor member.

In another example, the delivery wire is moveable within the inner lumen and the self-expanding element, and the dual function bump member and the pusher bump member are configured to engage at least one of the proximal and distal anchor members when the delivery wire is translated longitudinally. Also a force applied longitudinally to the delivery wire is transmitted through at least one of the bump members to at least one of the anchor members to move the self-expanding element through the catheter when the self-expanding element is in the compressed configuration within the catheter.

Further, when the delivery wire is moved distally, the dual function bump member contacts the distal anchor member and the pusher bump member does not contact the proximal anchor member during an initial deployment phase. Then, when the delivery wire is moved distally and the distal end of the self-expanding element is outside the catheter and expanded and the proximal end of the self-expanding element is still in the compressed configuration, the pusher bump member contacts the proximal anchor member and the dual function bump member does not contact the distal and the proximal anchor members during a final deployment phase. After the final deployment phase, the self-expanding element is in the expanded configuration.

An example of a recapture phase can occur when the distal end of the self-expanding element is outside the catheter and expanded and the proximal end of the self-expanding element is still in the compressed configuration. When the delivery wire is moved proximally the dual function bump member contacts the proximal anchor member and the pusher bump member does not contact the proximal anchor member during. Also, after the recapture phase, the self-expanding element is in the compressed configuration inside the catheter.

An example of a method of deploying a self-expanding element with a catheter, delivery wire and the self-expanding element including distal and proximal anchor members thereon, the steps include disposing a dual function bump member on the delivery wire between the proximal and distal anchors and disposing a pusher bump member outside of the self expanding element proximal of the proximal anchor. To deploy the self-expanding element, a user distally moves the delivery wire and engages the dual function bump member to the distal anchor member and unengages the pusher bump member. Next, the pusher bump member can be engaged to the proximal anchor member and disengaging the dual function bump member, thus, fully deploying the self-expanding element. As used in the example herein, "unengaging" connotes that in the first instance when the dual function bump is engaged, the pusher bump is not engaged with the proximal anchors and never engages with the distal anchors. Also, that the when the dual function bump is engaged, the pusher bump is not engaged either during deployment or recapture.

Another example to recover a partially deployed self-expanding element has the steps of proximally moving the delivery wire and engaging the dual function bump member to the proximal anchor member and disengaging the pusher bump member.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention. The drawing figures depict one or more implementations in accord with the present teachings, by way of example only, not by way of limitation.

FIG. 1 is an enlarged partial cross-sectional view of an apparatus for delivering and releasing a self-expanding element to a treatment site in a patient's body lumen, according to an example of the invention;

FIG. 2 is an enlarged partial cross-section view of the system apparatus within the body lumen and the self-expanding element in the compressed configuration;

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 3:
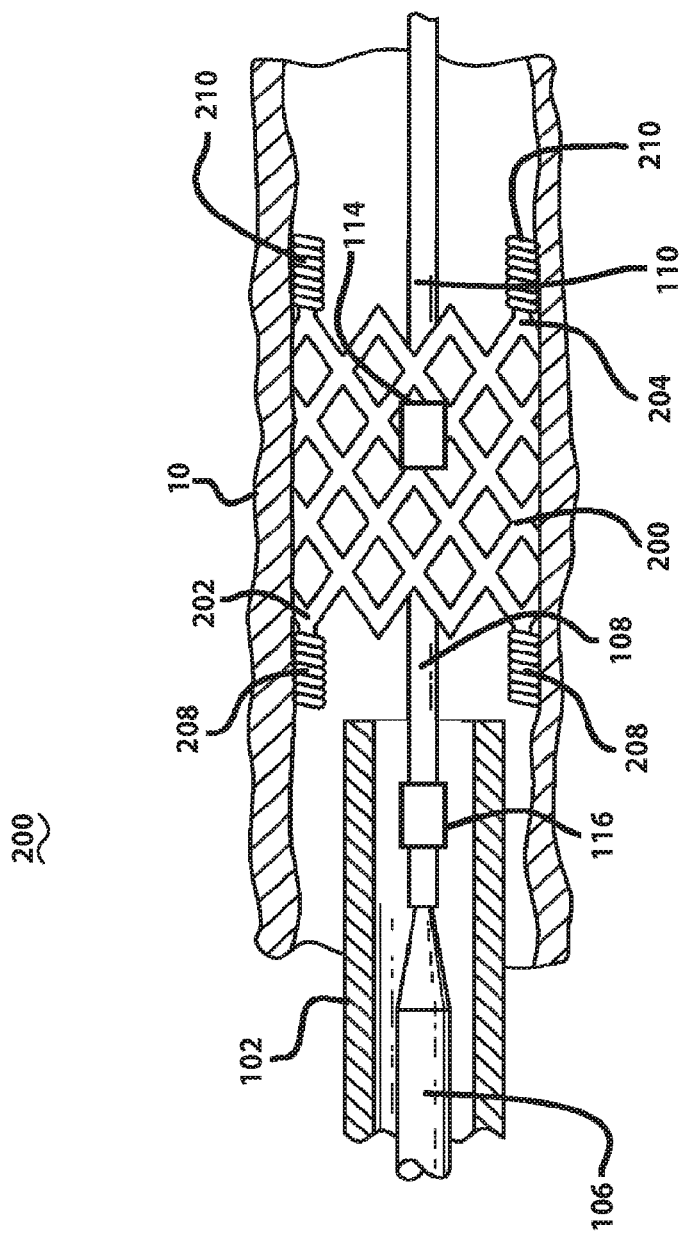
FIG. 3 is a cross-section view illustrating an expanded configuration of the self-expanding element within the patient's body lumen.
Figure 4:
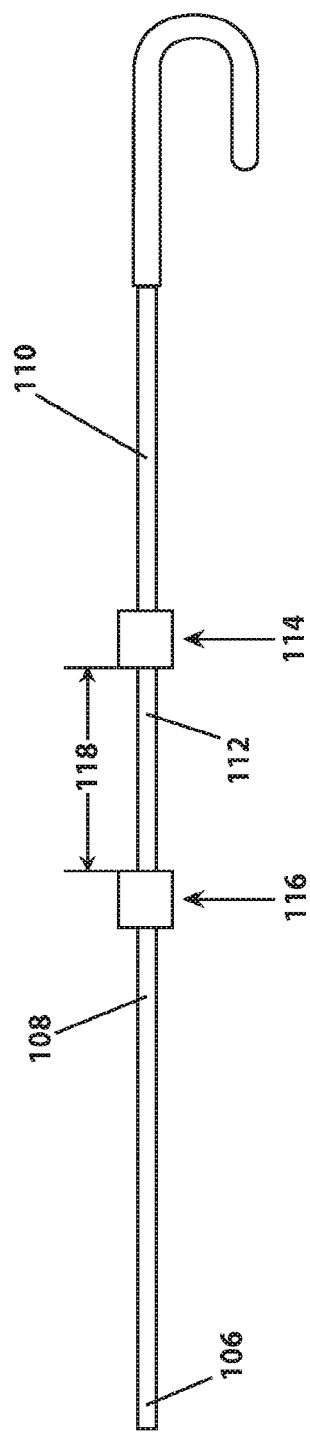
FIG. 4 is a section of the delivery wire with the dual function bump member and pusher bump member.
Figure 5:
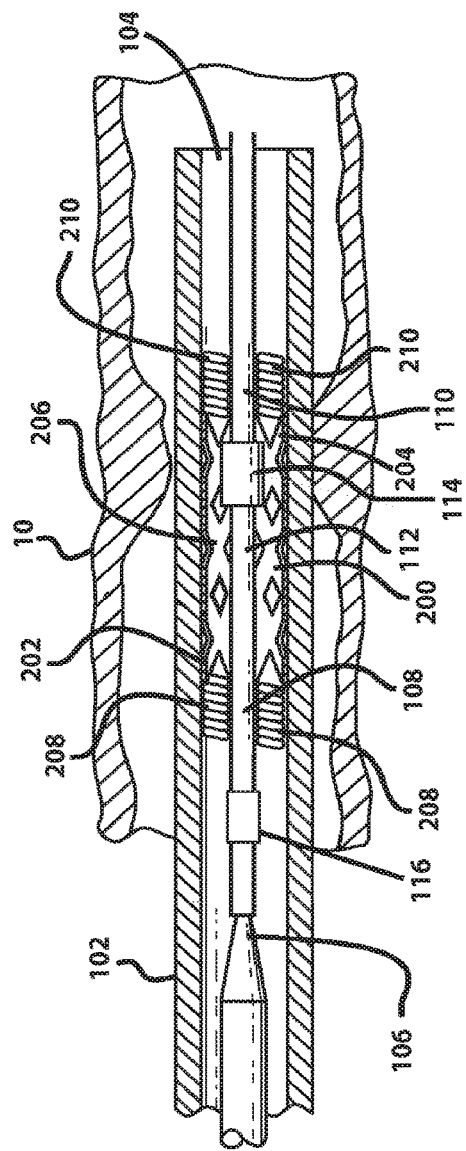
FIG. 5 is an enlarged partial cross-section view, similar to FIG. 2, with a portion of the self-expanding element cut away to expose the bump members on the delivery wire.

Examples of the present invention provide for an apparatus 100 that can deliver and release a self-expanding element 200 to a treatment site in a patient's body lumen (e.g. vasculature) 10. As is illustrated in FIG. 1-3, the apparatus 100 includes a catheter 102 having an inner lumen 104, the self-expanding element 200 can have an inner space (not illustrated), a proximal end 202, a distal end 204, and an intermediate section 206 located between the ends 202, 204. Typically, the self-expanding element 200 has a compressed configuration and an expanded configuration. In the compressed configuration, as illustrated in FIGS. 1 and 2, the self-expanding element 200 can be dimensioned to fit within the inner lumen 104 of the catheter 102. The catheter 102 can aid in constraining the self-expanding element 200 so it does not expand when contained within the catheter 102. Other elements can be used to constrain the self-expanding element 200 as are known in the art.

In the expanded configuration, as illustrated in FIG. 3, the self-expanding element 200 expands to fit the dimensions of the patient's body lumen 10. The expanded dimension of the self-expanding element 200 allows the apparatus 100 to pass therethrough, to either advance to a second location or be withdrawn. The self-expanding element 200 can be expandable under its inherent proprieties, based at least on its original shape and the nature of the materials that make up the element. Examples of the self-expanding element 200 can be one of pear shaped, ovoid, and elliptical when at its expanded diameter. The construction of the self-expanding element 200 is known to those of skill in the art.

The self-expanding element 200 can also include one or more anchor members 208, 210, such as proximal anchor members 208 at the proximal end 202 of the self-expanding element 200, and distal anchor members 210 disposed at the distal end 204 of the self-expanding element 200. The anchor members 208, 210 may be projections which extend generally parallel to a longitudinal axis of the self-expanding element 200 and extend downward toward the longitudinal axis of the self-expanding element 200. The anchor members 208, 210 can serves as a radiopaque marker for improved visualization during the deployment of the self-expanding element 200 within the body lumen 10. The anchor members 208, 210 can be used to align the self-expanding element 200 so it can be pushed and pulled through the catheter 102 without damage or deformation.

FIGS. 4-8 illustrate that the apparatus 100 can also include the delivery wire 106 disposed within and extending through the lumen 104 of the catheter 102. The delivery wire 106 has a proximal portion 108, a distal portion 110, and an intermediate portion 112 located between the proximal and distal portions 108, 110 of the delivery wire 106. The delivery wire 106 can have a dual function bump member 114 and a pusher bump member 116 extending radially outwardly from the delivery wire 106 and configured to engage the anchor members 208, 210 when the delivery wire 106 is translated longitudinally toward the one or more anchor members 208, 210. Force applied longitudinally to the delivery wire 106 can be transmitted through one or both of the bump members 114, 116 to the one or more anchor members 208, 210 to the self-expanding element 200. This acts to move the self-expanding element 200 through the catheter 102 when the self-expanding element 200 is constrained within the catheter 102. This is explained in more detail below.

As illustrated, the dual function bump member 114 is disposed between the proximal and distal anchor members 208, 210, toward the intermediate section 206 of the self-expanding element 200 and/or the intermediate portion 112 of the delivery wire 106. This places the dual function bump member 114 "inside" the self-expanding element 200. The pusher bump member 116 on the other hand, is disposed on the proximal portion 108 of the delivery wire 106, proximal to the proximal anchor members 208 of the self-expanding element 200. This places the pusher bump member 116 "behind" the self-expanding element 200. This placement facilitates both the deployment and retrieval of the self-expanding element 200 from the catheter 102 into the body lumen 10.

Figure 6:
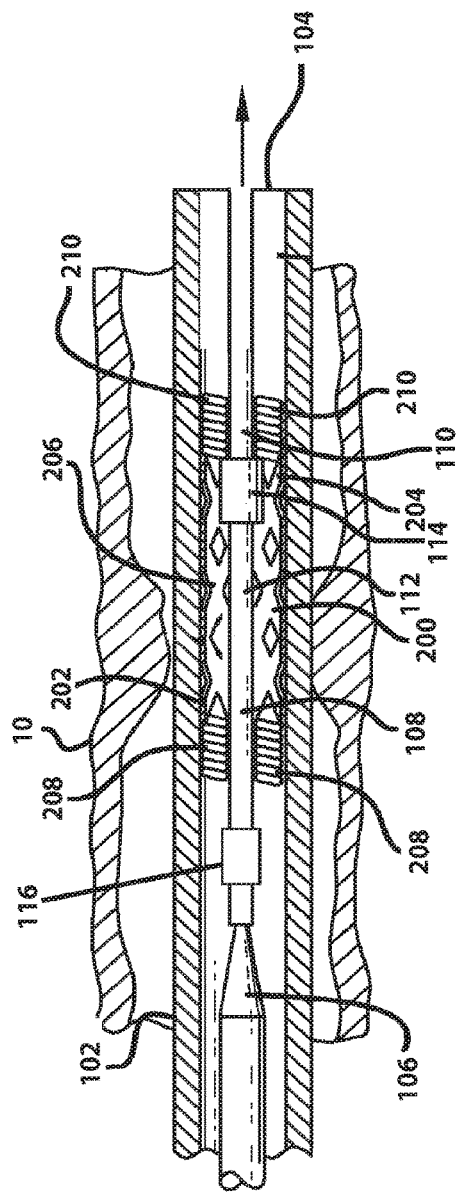
FIG. 6 is an enlarged partial cross-sectional view illustrating the initial deployment phase and pushing the self-expanding element distally.

Turning first to deployment, FIG. 6 illustrates the initial deployment phase. Here, as the delivery wire 106 is moved distally, the dual function bump member 114 contacts the distal anchor members 210 of the self-expanding element 200. In this phase, the dual function bump member 114 is pushing the self-expanding element 200 from the "inside." The pusher bump member 116 is not in contact with the proximal anchor members 208 during this phase. By having only the dual function bump member 114 pushing during the initial deployment phase there is reduced localized buckling and/or radial expansion of the self-expanding element 200. This reduces the force needed to drive the self-expanding element 200 distally out of the catheter 102.

Figure 7:
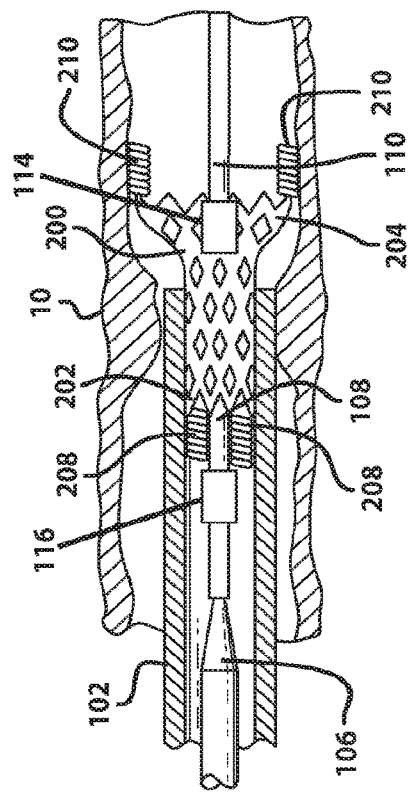
FIG. 7 is an enlarged partial sectional view of final deployment phase where the self-expanding element is moved distally with a proximal portion of the self-expanding stent compressed within a deployment catheter and a distal portion of the self-expanding stent expanded within the patient's body lumen.

In the final deployment phase, as illustrated in FIG. 7, the self-expanding element 200 is partially outside of the catheter 102 and partially expanded. The distal end 204 is expanded, while the proximal end 202 remains compressed. In the expanded state, the distal anchor members 210 have expanded away from both the delivery wire 106 and the dual function bump member 114. Now, the dual function bump member 114 no longer contacts the self-expanding element 200 and cannot apply distal or "forward" force to the self-expanding element 200. To deploy the remainder of the self-expanding element 200, the delivery wire 106 is advanced until the pusher bump member 116 contacts the proximal anchor members 208. The pusher bump member 116 is able to contact the proximal end 202 of the self-expanding element 200 since that section is still compressed inside the catheter 102. The pusher bump member 116 is "outside" of the self-expanding element 200 and pushes the remainder of the self-expanding element 200 completely outside the catheter 102. This allows the self-expanding element 200 to fully expand and be positioned inside the body lumen 10. Once fully expanded, the self-expanding element 200 has a larger diameter than the delivery wire 106, the bump members 114, 116 and the catheter 102, allowing this portion of the apparatus 100 to pass therethrough and be removed. This full deployment is illustrated in FIG. 3.

Given the above, the dual function bump member 114 and the pusher bump member 116 have a bump member distance 118 therebetween. The bump member distance 118 can be calibrated based on the size of the self-expanding element 200. The bump member distance 118 needs to be such that only one of the bump members 114, 116 contacts the anchor members 208, 210 at a given time when the delivery wire 106 is being moved either proximally or distally. Said another way, when the dual function bump member 114 contacts one set of the anchor members 208, 210, the pusher bump member 116 is not in contact with the proximal anchor members 208. Then, when the pusher bump member 116 is in contact with the proximal anchor members 208, the dual function bump member 114 is not in contact with either the distal anchor members 110 or the proximal anchor members 208. Another example of the bump member distance 118 is that it must be greater than a distance from the proximal piece of the distal anchor member 210 and the proximal piece of the proximal anchor member 208.

Figure 8:
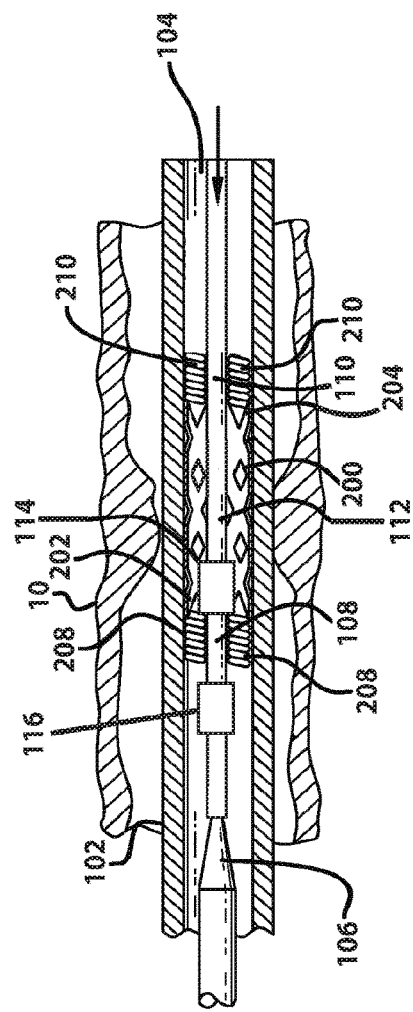
FIG. 8 is an enlarged partial cross-sectional view illustrating the recapture phase of pulling the self-expanding element proximally into the catheter.

In some instances, the self-expanding element 200 needs to be recaptured before full deployment. Once reason for recapture can be that the self-expanding element 200 needs to be better placed within the body lumen 10. FIG. 8 illustrates the recapture phase. Here, the self-expanding element 200 is pulled back/recaptured into the catheter 102 when the delivery wire 106 is pulled proximally. The dual function bump member 114 now moves proximally away from the distal anchor members 210 to engage the proximal anchor members 208. This engagement now pushes the proximal anchor members 208 proximally and forces the self-expanding element 200 to compress back into the catheter 102 until it is again fully enclosed in the inner lumen 104 of the catheter 102. During the recapture phase, the pusher bump member 116 does not contact the proximal anchor members 208 or the self-expanding element 200.

Figure 9:
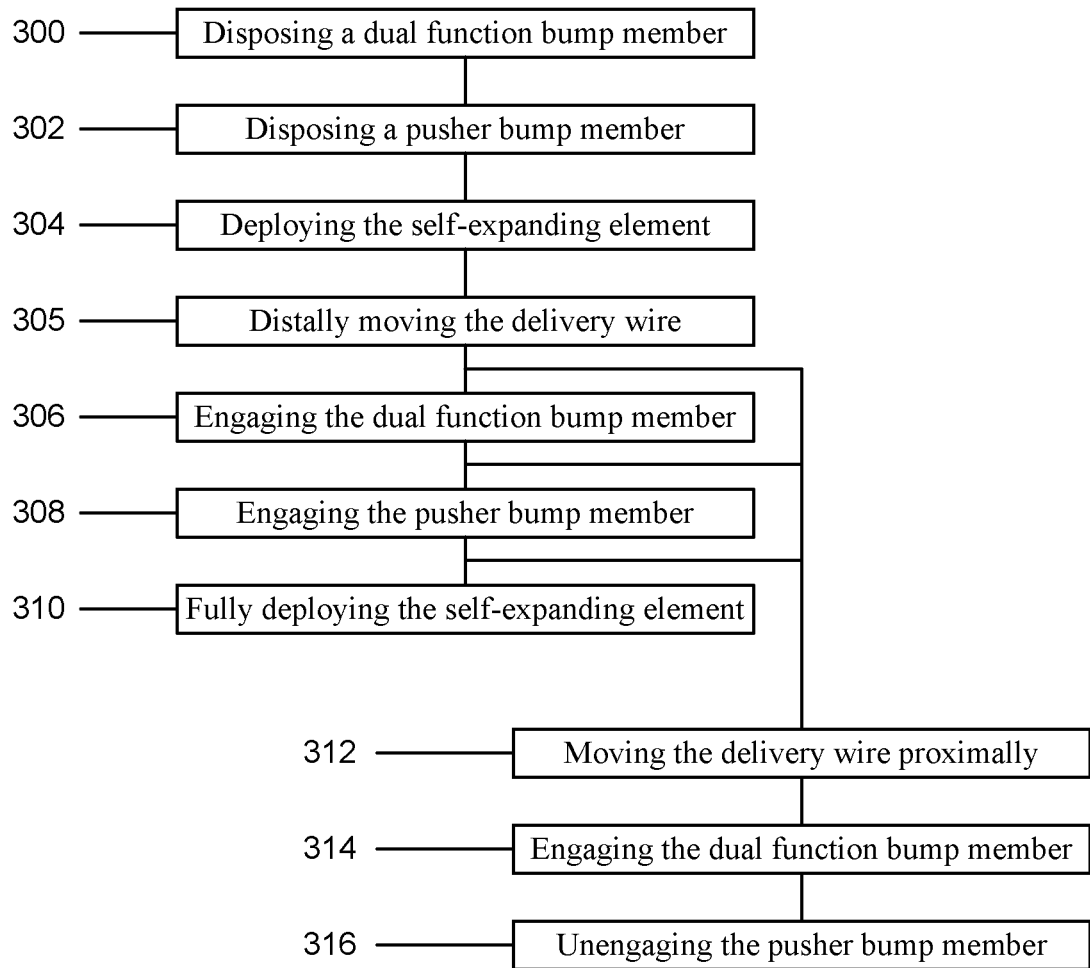
FIG. 9 is a flow diagram illustrating an example of a method of using the apparatus of the present invention.

FIG. 9 illustrates an example of the method of the present invention. In an apparatus 100 as described above, a dual function bump member 114 can be disposed between proximal and distal anchors 208, 210 of a self expanding element 200 (step 300). A pusher bump member 116 can be disposed outside of the self expanding element 200 on the proximal side (step 302). The self-expanding element 200 can be deployed (step 304) by distally moving the delivery wire 106 (step 305) till engaging the dual function bump member 114 to the distal anchor members 210 while the pusher bump member 116 remains unengaged (step 306). Next, the dual function bump member 114 is disengaged when the pusher bump member 116 engages the proximal anchor members 208 of the self-expanding element 200 (step 308). Finally, the self-expanding element 200 is fully deployed and the apparatus 100 can be removed (step 310).

In a recapture method example, any time before full deployment, the self-expanding element 200 can be recovered into the catheter 102. This includes the step of moving the delivery wire 106 proximally (step 312) to engage the dual function bump member 114 to the proximal anchor member 208 (step 314) while the pusher bump member 116 is unengaged (step 316).

Note that certain features of the apparatus 100 can be formed from materials that have a shape memory structure. For example, a metal alloy such as nickel titanium (NiTi), also known as Nitinol. Other elements may be formed of a non-superelastic material, such as spring steel or MP35N, an alloy of 35% nickel, 35% cobalt, 20% chromium, and 10% molybdenum, by weight. Features may be laser cut from the material, secure onto the delivery wire, or the delivery wire can be grinded down to create the above described elements.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A self-expanding element delivery apparatus, comprising:
   a catheter comprising an inner lumen;
   a self-expanding element comprising:
      a proximal end;
      a distal end;
      an intermediate portion located between the proximal end and the distal end;
      a proximal anchor member disposed at the proximal end;
      a distal anchor member disposed at the distal end;
      a compressed configuration dimensioned to fit within the inner lumen of the catheter; and
      an expanded configuration dimensioned larger than the catheter;
      wherein the self-expanding element is in the compressed configuration when disposed within the inner lumen, and
      wherein the self-expanding element is in the expanded configuration when disposed outside the inner lumen;
   a delivery wire disposed within and extending through the inner lumen and the self-expanding element, comprising:
      a proximal portion consisting of a pusher bump member disposed approximate to the proximal portion of the delivery wire, the pusher bump member being proximal of the proximal anchor member and unengaged to the self-expanding element;
      a distal portion;
      an intermediate portion located between said proximal and distal portions of the delivery wire, consisting of a dual function bump member disposed approximate to the intermediate portion of the delivery wire, the dual function bump member being confined inside the self-expanding element by the proximal anchor member and the distal anchor member; and
      a bump member distance between the dual function bump member and the pusher bump member so that only one of the dual function bump member and the pusher bump member can contact one of the distal anchor member and the proximal anchor member.

2. The self-expanding element delivery apparatus of claim 1,
   wherein the delivery wire is moveable within the inner lumen and the self-expanding element.

3. The self-expanding element delivery apparatus of claim 2,
   wherein the dual function bump member can engage both the proximal and distal anchor members when the self-expanding element is in the compressed configuration and the delivery wire is translated longitudinally.

4. The self-expanding element delivery apparatus of claim 2,
   wherein the dual function bump member and the pusher bump member are configured to engage at least one of the proximal and distal anchor members when the delivery wire is translated longitudinally.

5. The self-expanding element delivery apparatus of claim 2,
   wherein force applied longitudinally to the delivery wire is transmitted through at least one of the bump members to at least one of the anchor members to move the self-expanding element through the catheter when the self-expanding element is in the compressed configuration within the catheter.

6. The self-expanding element delivery apparatus of claim 2,
   wherein when the delivery wire is moved distally, the dual function bump member contacts only the distal anchor member and the pusher bump member does not contact the proximal anchor member during an initial deployment phase, and
   wherein the pusher bump member is unengaged to the stent while the dual function bump pushes the distal anchor member distally.

7. The self-expanding element delivery apparatus of claim 6,
   wherein when the delivery wire is moved distally and the distal end of the self-expanding element is outside the catheter and expanded and the proximal end of the self-expanding element is still in the compressed configuration, the pusher bump member contacts the proximal anchor member and the dual function bump member does not contact the distal and the proximal anchor members during a final deployment phase.

8. The self-expanding element delivery apparatus of claim 7,
   wherein after the final deployment phase, the self-expanding element is in the expanded configuration.

9. The self-expanding element delivery apparatus of claim 6,
   wherein the distal end of the self-expanding element is outside the catheter and expanded and the proximal end of the self-expanding element is still in the compressed configuration, when the delivery wire is moved proximally the dual function bump member contacts the proximal anchor member and the pusher bump member does not contact the proximal anchor member during a recapture phase, and
   wherein the pusher bump member is unengaged to the stent while the dual function bump member pushes the proximal anchor member proximally.

10. The self-expanding element delivery apparatus of claim 9, wherein after the recapture phase, the self-expanding element is in the compressed configuration inside the catheter.

11. The self-expanding element delivery apparatus of claim 9,
wherein when the delivery wire is moved proximally after the recapture phase, the dual function bump member contacts only the proximal anchor member and the pusher bump member does not contact the proximal anchor member.

12. The self-expanding element delivery apparatus of claim 1,
the anchor members comprising projections which extend generally parallel to a longitudinal axis of the self-expanding element and extend downward toward the longitudinal axis of the self-expanding element.

13. The self-expanding element delivery apparatus of claim 1,
the pusher bump member disposed proximal to the self-expanding element.

* * * * *